(12) United States Patent
Wu et al.

(10) Patent No.: US 10,799,271 B2
(45) Date of Patent: Oct. 13, 2020

(54) LOW PROFILE SCREW BASE AND ASSEMBLY METHOD FOR POSITIONING COMPRESSION RING

(71) Applicant: SHANDONG WEIGAO ORTHOPEDIC DEVICE COMPANY LTD, Weihai (CN)

(72) Inventors: Chunhui Wu, Weihai (CN); Jianguo Zhang, Weihai (CN); Ning Xie, Weihai (CN); Yajun Gao, Weihai (CN); Haichen Cong, Weihai (CN)

(73) Assignee: SHANDONG WEIGAO ORTHOPEDIC DEVICE COMPANY LTD, Weihai (CN)

( * ) Notice: Subject to any disclaimer, the term of this patent is extended or adjusted under 35 U.S.C. 154(b) by 270 days.

(21) Appl. No.: 15/571,853

(22) PCT Filed: Apr. 29, 2016

(86) PCT No.: PCT/CN2016/080783
§ 371 (c)(1),
(2) Date: Nov. 6, 2017

(87) PCT Pub. No.: WO2016/177304
PCT Pub. Date: Nov. 10, 2016

(65) Prior Publication Data
US 2018/0092666 A1    Apr. 5, 2018

(30) Foreign Application Priority Data

May 6, 2015    (CN) .......................... 2015 1 0225967

(51) Int. Cl.
*A61B 17/70*    (2006.01)
*A61B 17/00*    (2006.01)

(52) U.S. Cl.
CPC ...... *A61B 17/7032* (2013.01); *A61B 17/7037* (2013.01); *A61B 17/7046* (2013.01); *A61B 2017/00526* (2013.01)

(58) Field of Classification Search
CPC ........................ A61B 17/7037; A61B 17/7032
See application file for complete search history.

(56) References Cited

U.S. PATENT DOCUMENTS 5,443,467 A * 8/1995 Biedermann ...... A61B 17/7032
606/65
6,248,105 B1 * 6/2001 Schlapfer ........... A61B 17/7032
606/266

(Continued)

FOREIGN PATENT DOCUMENTS

CN    103099661 A    5/2013
CN    104783886 A    7/2015

(Continued)

*Primary Examiner* — David W Bates
(74) *Attorney, Agent, or Firm* — Kilpatrick Townsend & Stockton, LLP

(57) ABSTRACT

The low profile screw base comprises a screw base body and a positioning compression ring. An assembly hole penetrates longitudinally through the screw base body. A U-shaped slot for a connecting rod to pass through is provided on an upper portion of the screw base body. The inner wall of the screw base body on the opposite sides of the U-shaped slot is provided with internal threads. Snapping protrusions are formed on the inner wall of the screw base body on the opposite sides of the U-shaped slot below the internal threads. A lower ball socket matched with the round head of the ball screw is arranged in the assembly hole of the lower portion of the screw base body. The positioning compression ring used for compressing the round head is snap fitted above the lower ball socket and below the snapping protrusions (6).

3 Claims, 4 Drawing Sheets

(56) References Cited

U.S. PATENT DOCUMENTS

| | | | |
|---|---|---|---|
| 7,081,116 B1* | 7/2006 | Carly | A61B 17/7032 606/264 |
| 9,480,517 B2* | 11/2016 | Jackson | A61B 17/7037 |
| 9,848,916 B2* | 12/2017 | Biedermann | A61B 17/7037 |
| 2004/0049196 A1 | 3/2004 | Jackson | |
| 2008/0045953 A1* | 2/2008 | Garamszegi | A61B 17/7032 606/86 A |
| 2008/0287998 A1* | 11/2008 | Doubler | A61B 17/7037 606/269 |
| 2012/0143266 A1 | 6/2012 | Jackson et al. | |
| 2012/0179209 A1 | 7/2012 | Biedermann et al. | |
| 2013/0046350 A1 | 2/2013 | Jackson et al. | |
| 2013/0096620 A1* | 4/2013 | Biedermann | A61B 17/70 606/279 |
| 2013/0197586 A1* | 8/2013 | Matthis | A61B 17/7002 606/278 |
| 2014/0321945 A1* | 10/2014 | Black | F16B 29/00 411/383 |

FOREIGN PATENT DOCUMENTS

| | | |
|---|---|---|
| CN | 201600642 U | 9/2015 |
| CN | 204600651 U | 9/2015 |
| WO | 2011127065 A1 | 10/2011 |

* cited by examiner

LOW PROFILE SCREW BASE AND ASSEMBLY METHOD FOR POSITIONING COMPRESSION RING

CROSS-REFERENCE TO RELATED APPLICATIONS

The present application is a national phase entry under 35 USC § 371 of International Application PCT/CN2016/080783, filed Apr. 29, 2016, which claims the benefit of and priority to Chinese Patent Application No. 201510225967.4, filed May 6, 2015, the entire disclosures of which are incorporated herein by reference.

TECHNICAL FIELD

The present disclosure relates to the technical field of pedicle screw for orthopedic surgery. More particularly, it relates to a low-profile screw base with a small diameter and a low profile, and an assembly method for positioning compression ring.

BACKGROUND

There are generally three types of existing pedicle screws, that is, uniaxial pedicle screw, polyaxial pedicle screw, and uniplanar pedicle screw. The existing polyaxial pedicle screw and uniplanar pedicle screw each consists of a ball screw and a screw base cooperating with the ball screw, wherein the screw base comprises a screw base body and a positioning compression ring. A longitudinally through assembly hole is provided in the screw base body, and the upper portion of screw base body is provided with a U-shaped slot for a connecting rod to go through. An internal thread is provided on the inner wall of the screw base body, at both sides of the U-shaped slot; snapping protrusions are also provided on the inner wall of the screw base body, at both sides of the U-shaped slot and beneath the internal thread. A lower ball socket matching with the ball head of the ball screw is provided inside the assembly hole on the lower portion of the screw base body, and a positioning compression ring for compressing and positioning the ball head of the ball screw is provided above the lower ball socket and below the snapping protrusion.

The structure of the existing positioning compression ring is such that a cylindrical ring body is provided, wherein a lower end of the ring body is provided with an upper ball socket matching with the ball head of the ball screw and an upper end of the ring body is planar or provided with an U-shaped (also referred to as a saddle-shaped) rod-receiving groove matching with an connecting rod ring bodyring bodyring body

SUMMARY

Technical Problem

Due to the planar top, the positioning compression ring only need to position longitudinally, so that the design of cooperating for the compression ring and screw base is relatively simple. However, the contact with the round connecting rod is a line contact, so it is easy to sink down in use, while the contact surface with the rod is small, rendering a poorer fixing effect compared with a U-shaped positioning ring. The rod-containing groove of the U-shaped positioning compression ring and the connecting rod fit each other tightly with a good fixing effect. However, it is necessary to prevent both the drawing back upward and longitudinal rotation of the compression ring after the screw assembly of the compression ring, or otherwise the rod-containing groove may dislocate from the U-shaped slot of the screw base, resulting in malfunction.

The technical solution used by the existing positioning ring for preventing the drawing back upward is that: a position-limiting flange that protrudes outward and matches with the snapping protrusion is provided on the upper portion of the ring body at the left and right sides of the rod-containing groove convex ring, wherein the lower side surface of the position-limiting flange is an slope. During assembly, the positioning compression ring is placed downward into the upper portion of the snapping protrusion from above the assembly hole, punching the positioning compression ring downward, so that the slope on the lower side of the position-limiting flange applies a force on the ring body on both left and right sides of the rod-containing groove, causing the ring body to have an elastic deformation and insert into the lower side of the snapping protrusion. The positioning compression ring with the above-mentioned structure and the assembly method thereof result in an screw base body having a large outer diameter, a large profile, a thin side wall, and low strength.

The rotation preventing structure of the existing positioning compression ring is a side-stamping bump positioning structure. In this structure, first a hole must be punched on a side of the screw base, and then a ball screw and a positioning compression ring are installed in turn from the upper side of the screw base. The side of the positioning compression ring is provided with an inward groove, and the bottom of the side hole on the screw base is stamped inwardly using a punch or other tools to deform and generate a protrusion, which enters into the side groove of the positioning compression ring. The protrusion and the positioning compression ring can prevent the compression ring from drawing back upward and longitudinal rotation at the same time. The stamping deformation is not easy to control precisely in the assembly process, and the drilling depth on the side of the screw base varies in a range of tolerance. Therefore, the height and thickness of the protrusion can vary during manufacture. If the height and thickness of the protrusion are too small, the screwdriver may bring out the positioning compression ring easily during the intraoperative operation, which may lead to loss and failure of the screw parts. Moreover, since the shape of the protrusion is circular, if the upward pull-force from the screwdriver is too large, the protrusion may be easily pushed back to the side holes of the screw base, which causes the disassembly of the screws already implanted in the human body. Such problems often occur during surgery, which brings great risks for the safety of surgery. Moreover, the side wall of the screw base and the side surface of the positioning compression ring are the stress-bearing part, which is highly stressed after screwing, while the side hole and groove can both affect the strength of the screw. Therefore, in order to meet the strength requirements for using, the size of the screw base is usually large, which has a negative impact on the healing of the surrounding tissue of the patient.

Technical Solution

One object of the present disclosure aims to solve the above-mentioned deficiencies of the prior art and provides a low-profile screw base and assembly method for a positioning compression ring, wherein the low-profile screw base has a simple structure, convenient assembly process, a small outer diameter of the screw base body, a thick side wall and high strength of the thread portion of the screw base body, and a safe and reliable positioning compression ring.

The technical solution of the present disclosure to solve the above-mentioned deficiencies of the prior art is that:

A low profile screw base comprises a screw base body and a positioning compression ring, wherein the screw base body is provided with: a longitudinally through assembly hole inside the screw base body; a U-shaped slot for the connecting rod to go through on the upper portion of the screw base body; an internal thread on the internal wall of the screw base body, on both sides of the U-shaped slot; a snapping protrusion on the internal wall of the screw base body, under the internal thread on both sides of the U-shaped slot; a lower ball socket matching with a ball head of a ball screw, provided in the assembly hole on the lower portion of the screw base body; and, a positioning compression ring for compressing and positioning the ball head of the ball screw, provided above the lower ball socket and under the snapping protrusion. The structure of the positioning compression ring is provided with a ring body with a cylindrical shape, wherein the ring body is provided with an upper ball socket matching with the ball head of the ball screw on an lower end of ring body and a rod-containing groove matching with a connecting rod on an upper end of the ring body, characterized in that a groove for containing a position-limiting flange of the positioning compression ring is provided above the snapping protrusion, with the inner diameter of the groove greater than the diameter of the position-limiting flange of the positioning compression ring; a position-limiting flange that protrudes outward and matches with the snapping protrusion is provided on the upper portion of the ring body on both left and right sides of the rod-containing groove; an outwardly-protruding rotation-preventing lug is provided on the outer wall of the ring body, on the upper side or lower side of the position-limiting flange, the rotation-preventing lug having a strip shape and longitudinally provided on the outer wall of the ring body; and, the snapping protrusion (and the inner wall of the screw base body) is provided with a rotation-preventing groove matching with the rotation-preventing lug.

The rotation-preventing groove according to the present disclosure is provided at the middle portion of the snapping protrusion and runs through the snapping protrusion from upper to lower side to divide the snapping protrusion into a left section and a right section.

An assembly method for positioning compression ring of a low-profile screw base of a pedicle screw is provided, wherein it comprises the following steps:

a. placing a positioning compression ring right above a body of the screw base, allowing position-limiting flanges provided on a ring body and located on the left and right sides of the rod-containing groove of the positioning compression ring to face two U-shaped slots located in the screw base body;

b. placing the positioning compression ring downward into the screw base body from above an assembly hole, c. rotating the positioning compression ring when the two position-limiting flanges and rotation-preventing lug on the positioning compression ring reach the groove located between an internal thread and a snapping protrusion on an inner wall of the screw base body, so that the position-limiting flange and the rotation-preventing lug rotate into the groove located between the internal thread and the snapping protrusion of the inner wall of the screw base body and the rotation-preventing lug is facing the rotation-preventing groove; and d. punching the positioning compression ring downward to apply a force on the ring body so that the ring body has an elastic deformation, the position-limiting flange inserts beneath the snapping protrusion, and the rotation-preventing lug inserts into the rotation-preventing groove.

Advantageous Effects

According to the present disclosure, the position-limiting flange is where the largest radial diameter of the positioning compression ring occurs. With the above-mentioned method, the assembly of the positioning compression ring does not need to pass through the internal thread of the inner wall of the screw base body, and when the thickness of the inner wall is constant, the diameter of the screw base body is small. Small-size screws have great significance to Asian patients with small body size, especially for women and adolescents, because of relatively small stimulation to the surrounding tissue from the screw base, which is more conducive to postoperative healing. When the outer diameter of the screw base body is constant, the thick side wall and high strength of the screw base body improve the safety and reliability of the screw base body. The rotation-preventing lug and rotation-preventing groove for anti-rotation are simple in structure and easy to use. Since there are four sections of long-range interference fit between the limiting lug and the snapping protrusions of the screw base, it is safer and more reliable compared with the prior art and can prevent disengagement of the screws caused by the pulling out of the positioning compression ring during operation.

DETAILED DESCRIPTION

Figure 1:
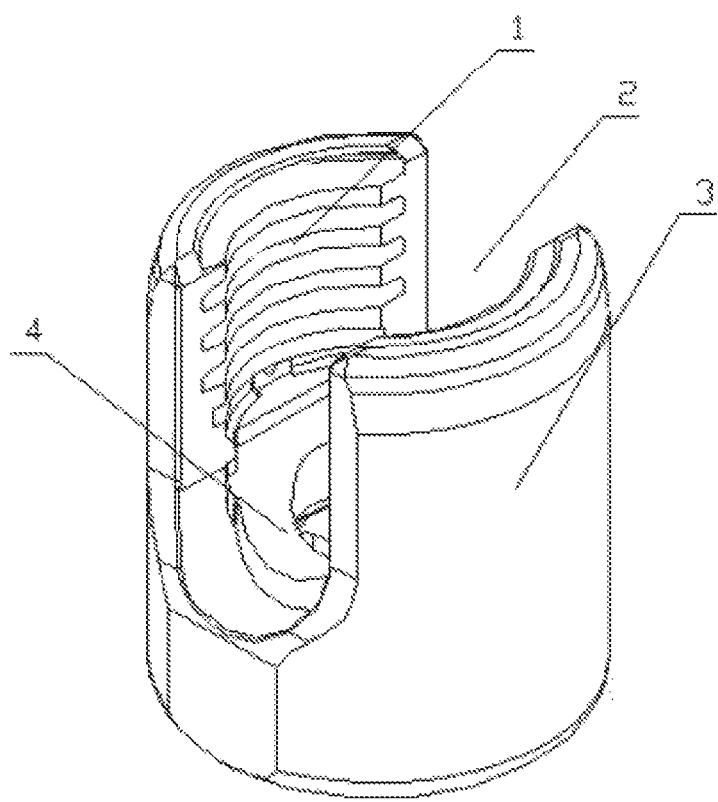
FIG. 1 is a schematic structural view of the present disclosure.
Figure 2:
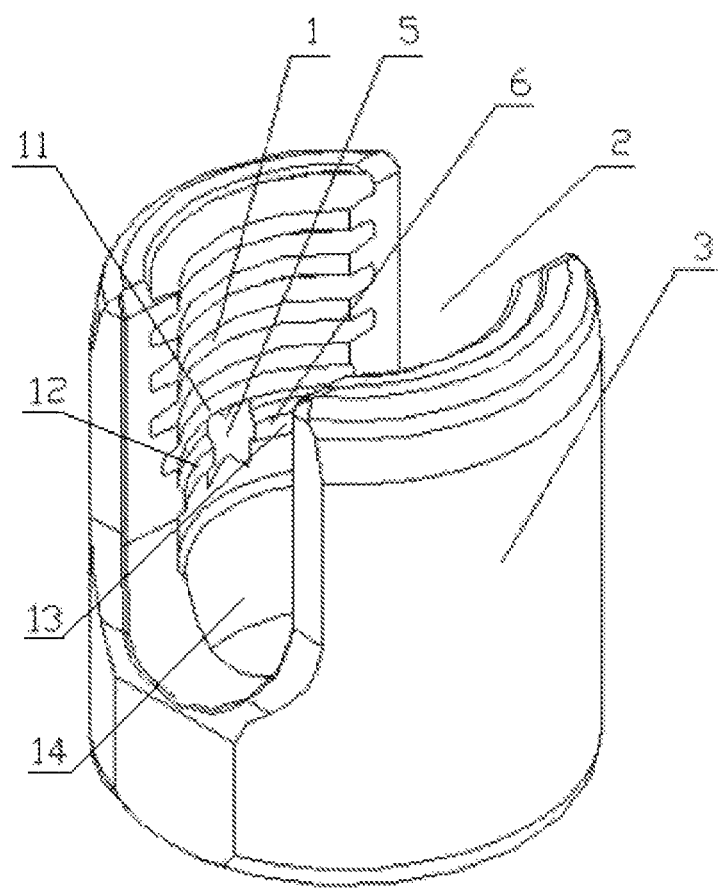
FIG. 2 is a schematic structural view of the screw base body according to the present disclosure.
Figure 3:
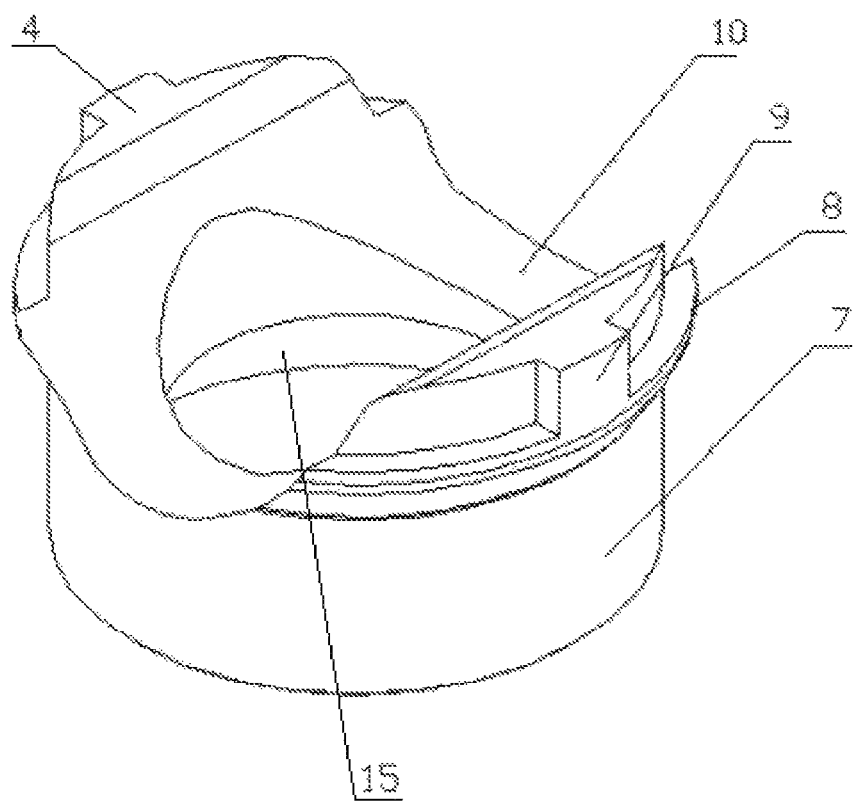
FIG. 3 is a schematic structural view of the positioning compression ring according to present disclosure.
Figure 4:
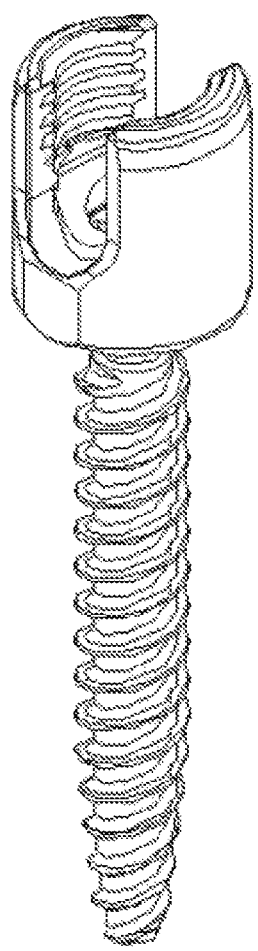
FIG. 4 is a schematic assembly structural view of the ball screw according to present disclosure.

As shown in FIG. 1-3, a low profile screw base is provided, comprising a screw base body 3 and a positioning compression ring 4, wherein the screw base body 3 is provided with: a longitudinal through assembly hole inside the screw base body 3; a U-shaped slot 2 for the connecting rod to go through on the upper portion of the screw base body; an internal thread 1 on the internal wall of the screw base body 3, on both sides of the U-shaped slot 2; a snapping protrusion 6 on the internal wall of the screw base body, under the internal thread 1 on both sides of the U-shaped slot; a lower ball socket 14 matching with a ball head of a ball screw, provided in the assembly hole on the lower portion of the screw base body; and, a positioning compression ring 4 for compressing and positioning the ball head of the ball screw, provided above the lower ball socket 14 and under the snapping protrusion 6. The structure of the positioning compression ring 4 is provided with a ring body 7 with a cylindrical peripheral shape, wherein the ring body 7 is provided with an upper ball socket 15 matching with the ball head of the ball screw on a lower end of ring body 7 and a rod-containing groove 10 matching with a connecting rod on an upper end of the ring body 7. The present disclosure is characterized in that: a groove 11 for containing a position-limiting flange of the positioning compression ring is provided above the snapping protrusion, with the inner diameter of the groove greater than the diameter of the position-limiting flange of the positioning compression ring; a position-limiting flange 8 that protrudes outward and matches with the snapping protrusion 6 is provided peripherally on the upper and middle portions of the ring body 7 on both left and right sides of the rod-containing groove 10, wherein the position-limiting flange 8 has an arc shape and has a lower surface of a slope included outward from lower to upper side; an outwardly-protruding rotation-preventing lug 9 with a rectangular shape is provided axially on the ring body, on the upper side of the position-limiting flange; and, the snapping protrusion 6 and the inner wall of the screw base body are provided with a rotation-preventing groove 5 matching with the rotation-preventing lug 9. As shown in FIG. 1-3, the rotation-preventing groove 5 is provided at the middle portion of the snapping protrusion and runs through the snapping protrusion from upper to lower side to divide the snapping protrusion into a left section 12 and a right section 13.

The above-mentioned assembly method for positioning compression ring of low-profile screw base, wherein it comprises the following steps:

a. placing a positioning compression ring right above a screw base body, allowing position-limiting flanges 8 provided on a ring body on the left and right sides of the rod-containing groove 10 of the positioning compression ring to face two U-shaped slots 2 located in the screw base body 3, with an angle of 90 degree;

b. placing the positioning compression ring downward into the screw base body from above an assembly hole, during which process the position-limiting flanges 8 move downward in the two U-shaped slots 2 located in the screw base body 3;

c. rotating the positioning compression ring 4 when the two position-limiting flanges 8 and rotation-preventing lug 9 on the positioning compression ring 4 move downward n the U-shaped groove to be between an internal thread and a snapping protrusion 6 on an inner wall of the screw base body, so that the position-limiting flange and the rotation-preventing lug rotate to be between the internal thread and the snapping protrusion of the inner wall of the screw base body where the rotation-preventing lug is facing the rotation-preventing groove; and d. punching the positioning compression ring 4 downward to apply a force on the ring body so that the ring body and the screw base body 3 has an elastic deformation, the position-limiting flange 8 inserts beneath the snapping protrusion 6, and the rotation-preventing lug 9 inserts into the rotation-preventing groove 5.

INDUSTRIAL UTILITY

According to the present disclosure, the position-limiting flange is where the largest radial diameter of the positioning compression ring occurs. With the above-mentioned method, the assembly of the positioning compression ring does not need to pass through the internal thread of the inner wall of the screw base body, and when the thickness of the inner wall is constant, the diameter of the screw base body is small, allowing a low profile during operation. When the outer diameter of the screw base body is constant, the thick side wall and high strength of the screw base body is made possible. The rotation-preventing lug and rotation-preventing groove for anti-rotation are simple in structure and easy to use, while allowing a good rotation-preventing performance. The rotation-preventing lug of the positioning compression ring can also be placed under of the position-limiting flange, while the corresponding rotation-preventing groove on the side wall of the screw base can also be extended downward accordingly as needed. Since the rotation-preventing lug is positioned far away from the opening of the rod-containing groove, it will not easily compress inward under stress, therefore the anti-rotation effect of this positioning compression ring is better. The rotation-preventing structures of both the rotation-preventing lug and the rotation-preventing groove are safe and reliable, which further reduce the size of the screw base, so that the profile is smaller and healing effect of the patient surrounding tissue is better.

What is claimed is:

1. A screw base, comprising:
   a screw base body and a positioning compression ring, wherein the screw base body is provided with:
   a through assembly hole, located in the screw base body;
   a U-shaped slot for a connecting rod to go through, located on a first portion of the screw base body;
   an internal thread, located on an internal wall of the screw base body, on both sides of the U-shaped slot;
   a snapping protrusion, located on the internal wall of the screw base body, below the internal thread and on both sides of the U-shaped slot; and,
   a first ball socket for matching with a ball head of a ball screw, provided in the assembly hole and at a second portion of the screw base body;
   wherein, the positioning compression ring is provided above the first ball socket and below the snapping protrusion, for compressing and positioning the ball head of the ball screw; wherein, the structure of the positioning compression ring is such that a ring body with a cylindrical shape is provided, and the ring body is provided with a second ball socket for matching with the ball head of the ball screw at a first end of the ring body and a rod-containing groove for matching with the connecting rod at a second end of the ring body; and
   wherein, a position-limiting flange that protrudes outward and matches with the snapping protrusion is provided on the second end of the ring body on both a first side and a second side of the rod-containing groove, an outwardly-protruding rotation-preventing lug is provided on an outer wall of the ring body and on one side of the position-limiting flange, and the snapping protrusion is provided with a rotation-preventing groove for matching with the rotation-preventing lug,
   wherein the rotation-preventing groove is provided at a middle portion of the snapping protrusion and runs through the snapping protrusion from side to side to divide the snapping protrusion into a first section and second section.

2. The screw base according to claim 1, wherein a groove for containing the position-limiting flange of the positioning compression ring is provided above the snapping protrusion, the groove having an inner diameter greater than a diameter of the position-limiting flange of the positioning compression ring.

3. A method for assembly of a positioning compression ring of a screw base according to claim 1, wherein the method comprises:
   placing the positioning compression ring above the screw base body, allowing the position-limiting flange provided on the ring body on the first and second sides of the rod-containing groove of the positioning compression ring to face the two U-shaped slots located in the screw base body;

placing the positioning compression ring downward into the screw base body from above the assembly hole, rotating the positioning compression ring when the position-limiting flange and rotation-preventing lug on the positioning compression ring move to be between the internal thread and the snapping protrusion on the inner wall of the screw base body, so that the position-limiting flange and the rotation-preventing lug rotate to be between the internal thread and the snapping protrusion of the inner wall of the screw base body where the rotation-preventing lug is facing the rotation-preventing groove; and punching the positioning compression ring downward to apply a force on the ring body so that the ring body has an elastic deformation, the position-limiting flange inserts beneath the snapping protrusion, and the rotation-preventing lug inserts into the rotation-preventing groove.

* * * * *